(12) United States Patent
Devarakonda et al.

(10) Patent No.: US 11,031,109 B2
(45) Date of Patent: Jun. 8, 2021

(54) CONTEXTUAL EMR BASED DASHBOARD GRAPHICAL USER INTERFACE ELEMENTS

(71) Applicant: International Business Machines Corporation, Armonk, NY (US)

(72) Inventors: Murthy V. Devarakonda, Peekskill, NY (US); Sarah Miller, Cambridge, MA (US); Paul C. Tang, Los Altos, CA (US)

(73) Assignee: International Business Machines Corporation, Armonk, NY (US)

( * ) Notice: Subject to any disclaimer, the term of this patent is extended or adjusted under 35 U.S.C. 154(b) by 339 days.

(21) Appl. No.: 15/857,114

(22) Filed: Dec. 28, 2017

(65) Prior Publication Data

US 2019/0206526 A1 Jul. 4, 2019

(51) Int. Cl.
*G16H 10/60* (2018.01)
*G16H 40/63* (2018.01)
(Continued)

(52) U.S. Cl.
CPC .......... *G16H 10/60* (2018.01); *G06F 3/0482* (2013.01); *G06F 40/106* (2020.01);
(Continued)

(58) Field of Classification Search
CPC ........ G16H 50/20; G16H 10/60; G16H 10/20; G16H 20/10; G16H 50/30; G16H 40/20;
(Continued)

(56) References Cited

U.S. PATENT DOCUMENTS 6,401,072 B1 * 6/2002 Haudenschild ..... G06F 19/3418
705/3
7,433,827 B2 10/2008 Rosenfeld et al.
(Continued)

OTHER PUBLICATIONS

List of IBM Patents or Patent Applications Treated as Related, Feb. 19, 2018, 2 pages.
(Continued)

*Primary Examiner* — Neal Sereboff
(74) *Attorney, Agent, or Firm* — Stephen R. Tkacs; Stephen J. Walder, Jr.; William J. Stock

(57) ABSTRACT

A mechanism is provided in a data processing system comprising a processor and a memory, the memory comprising instructions that are executed by the processor to specifically configure the processor to implement a relevant information graphical presentation engine for providing a graphical user interface (GUI) that presents information from a patient electronic medical record (EMR). The relevant information graphical presentation engine generates a GUI presenting patient EMR data pertinent to a condition of the patient. The relevant information graphical presentation engine identifies a change in treatment recorded in the patient EMR, submits a question to a healthcare cognitive system to query the patient EMR for a reason for the change in treatment, and receives at least one answer from the healthcare cognitive system identifying of a reason portion of the patient EMR that provides a reason for the change in treatment. The relevant information graphical presentation engine generates a GUI element that references the reason portion of the patient EMR and inserts the GUI element in the GUI in association with the information from the patient EMR pertinent to the outcome. The relevant information graphical presentation engine outputs the GUI to the healthcare professional.

20 Claims, 10 Drawing Sheets

(51) Int. Cl.
- *G06F 3/0482* (2013.01)
- *G06F 40/106* (2020.01)
- *G06F 40/216* (2020.01)
- *G06F 3/0484* (2013.01)
- *G06F 40/134* (2020.01)

(52) U.S. Cl.
CPC .......... *G06F 40/216* (2020.01); *G16H 40/63* (2018.01); *G06F 3/04842* (2013.01); *G06F 40/134* (2020.01)

(58) Field of Classification Search
CPC ........ G16H 50/70; G16H 40/63; G16H 15/00; G16H 20/40; G16H 50/50; G16H 40/67; G16H 40/40; G16H 70/60; G16H 80/00; G16H 20/60; G16H 20/70; G16H 50/80; G16H 70/20; G16H 70/40; G06Q 50/22; G06Q 50/24; G06Q 10/10; G06Q 30/0601; G06Q 10/06; G06Q 10/0631; G06Q 30/02; G06Q 40/02; G06Q 40/08; G06Q 10/00; G06Q 10/06313; G06Q 10/0637; G06Q 30/0282

See application file for complete search history.

(56) References Cited

U.S. PATENT DOCUMENTS

| | | | |
|---|---|---|---|
| 9,081,879 B2 | 7/2015 | Iliff | |
| 9,492,341 B2 | 11/2016 | Huster et al. | |
| 9,690,861 B2 | 6/2017 | Boloor et al. | |
| 2002/0065686 A1 | 5/2002 | Monteleone et al. | |
| 2004/0122701 A1 | 6/2004 | Dahlin et al. | |
| 2005/0159987 A1 | 7/2005 | Rosenfeld et al. | |
| 2006/0085223 A1* | 4/2006 | Anderson | G16H 20/17 705/2 |
| 2006/0122869 A9 | 6/2006 | Rosenfeld et al. | |
| 2009/0222286 A1* | 9/2009 | Elsholz | G16H 10/60 705/3 |
| 2009/0228303 A1 | 9/2009 | Faulkner et al. | |
| 2009/0281839 A1* | 11/2009 | Lynn | G16H 10/60 705/3 |
| 2012/0089419 A1 | 4/2012 | Huster et al. | |
| 2012/0215560 A1 | 8/2012 | Ofek et al. | |
| 2012/0239434 A1 | 9/2012 | Breslow et al. | |
| 2013/0226601 A1 | 8/2013 | Razmi et al. | |
| 2013/0226617 A1 | 8/2013 | Mok et al. | |
| 2014/0052465 A1* | 2/2014 | Madan | G06F 19/00 705/2 |
| 2014/0244309 A1 | 8/2014 | Francois | |
| 2014/0310016 A1 | 10/2014 | Kenney et al. | |
| 2014/0337052 A1* | 11/2014 | Pellini | G16H 10/60 705/3 |
| 2015/0058039 A1 | 2/2015 | Shiloh | |
| 2015/0066520 A1 | 3/2015 | Leon et al. | |
| 2015/0161241 A1 | 6/2015 | Haggar et al. | |
| 2015/0193583 A1 | 7/2015 | McNair et al. | |
| 2015/0261849 A1 | 9/2015 | Chu-Carroll et al. | |
| 2016/0019299 A1 | 1/2016 | Boloor et al. | |
| 2016/0019352 A1 | 1/2016 | Cohen et al. | |
| 2016/0098456 A1* | 4/2016 | Contreras | G06F 40/169 705/3 |
| 2016/0110523 A1 | 4/2016 | Francois | |
| 2016/0147727 A1* | 5/2016 | Allen | G16H 10/40 715/231 |
| 2017/0027787 A1 | 2/2017 | Huster et al. | |
| 2017/0178266 A1 | 6/2017 | Schmidt | |
| 2017/0185920 A1 | 6/2017 | Chawla et al. | |
| 2017/0286626 A1* | 10/2017 | Jayakumar | G16H 15/00 |
| 2019/0156921 A1 | 5/2019 | Kohli et al. | |

OTHER PUBLICATIONS

"The Era of Cognitive Systems: An inside look at IBM Watson and how it works", IBM Corporation, IBM Software Group, Whitepaper, IBM Watson Solutions, Sep. 2012, 19 pages.

Abedtash, Hamed, "An Interoperable Electronic Medical Record-Based Platform for Personalized Predictive Analytics", Indiana University-Purdue University Indianapolis (IUPUI), Doctor of Philosophy in the School of Informatics and Computing, Doctoral Dissertation, Jul. 2017, 184 pages.

Alemzadeh, Homa et al., "An NLP-based Cognitive System for Disease Status Identification in Electronic Health Records", IEEE, 2017 IEEE EMBS International Conference on Biomedical & Health Informatics (BHI), Feb. 16-19, 2017, 4 pages.

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.

Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.

Taranu, Ionut, "Data mining in healthcare: decision making and precision", Database Systems Journal, vol. VI, Issue Apr. 2015, Publication date: May 5, 2016, 8 pages.

* cited by examiner

FIG. 4A

| HYPERTENSION | DIABETES |

NOTES FROM LAST VISIT (20 Dec 2016)

Plan
- Will increase the losartan to 100mg qd
- Continue checking home BPs 3x/wk
- Let me know via online message if multiple BPs above 140/90
- RTC 1 mo

READ NOTE

HISTORY

```
        2016                                              2017
        May   Jun   Jul   Aug   Sep   Oct   Nov   Dec   Jan   Feb
        (PCP)       (H)   (PCP) (PCP)             (PCP) (TODAY)
```

ENCOUNTERS

OUTCOME

SUPPORTING MEASUREMENTS

LIFESTYLE

ANCILLARY MEASUREMENTS

FIG. 4E

| HISTORY | 2016 May | Jun | Jul | Aug | | | | Feb |
| ENCOUNTERS | (PCP) | | (H) | | | | | (TODAY) |
| MEDICATIONS | | | | | | | | |
| Losartan | | | | | | | | (max) |
| Lisinopril | 5 mg | | | 5 mg | | | | |

432 — Side Effect
Now elevated after patient discontinued his lisinopril due to development of a dry cough. The patient chose to discontinue the drug himself after reading about cough and lisinopril on the Internet. His cough resolved about a week later. Will assume that the cough was associated with his lisinopril (read note)

430

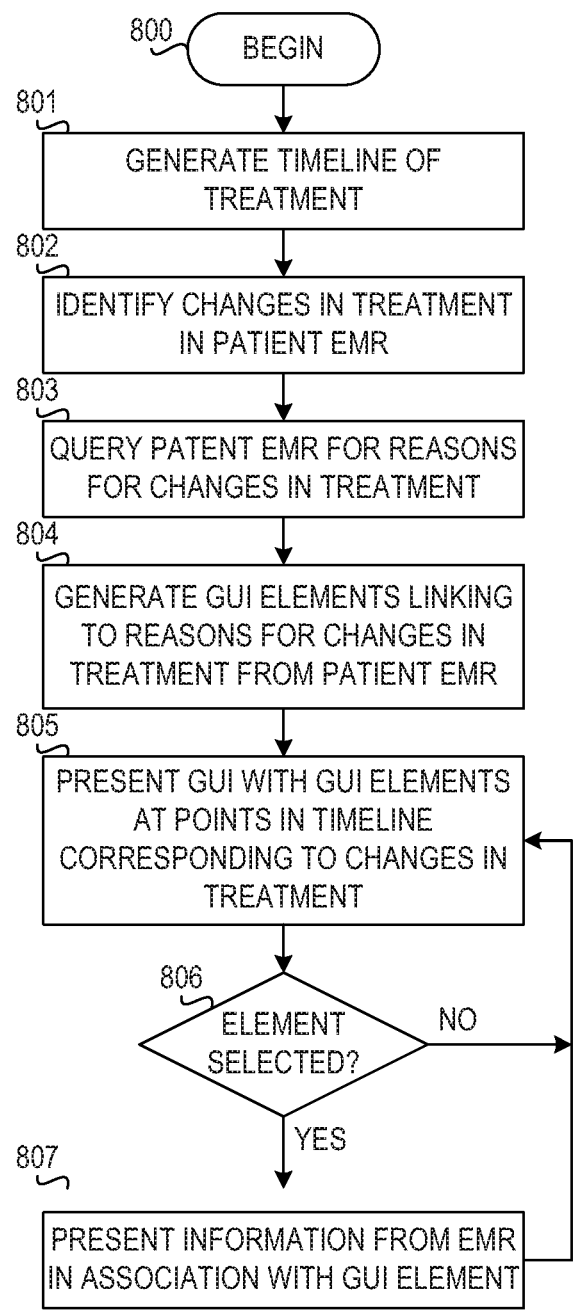

CONTEXTUAL EMR BASED DASHBOARD GRAPHICAL USER INTERFACE ELEMENTS

BACKGROUND

The present application relates generally to an improved data processing apparatus and method and more specifically to mechanisms for providing graphical presentation of relevant information from electronic medical records with contextual EMR-based dashboard GUI elements.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. It can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long term changes in a patient. Population-based studies of medical records may also be facilitated by the widespread adoption of EMRs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a relevant information graphical presentation engine for providing a graphical user interface (GUI) that presents information from a patient electronic medical record (EMR). The method comprises generating, by the relevant information graphical presentation engine executing in the data processing system, a GUI presenting patient EMR data pertinent to a condition of the patient. The method further comprises identifying, by the relevant information graphical presentation engine, a change in treatment recorded in the patient EMR, submitting, by the relevant information graphical presentation engine, a question to a healthcare cognitive system to query the patient EMR for a reason for the change in treatment, and receiving, by the relevant information graphical presentation engine, at least one answer from the healthcare cognitive system identifying of a reason portion of the patient EMR that provides a reason for the change in treatment. The method further comprises generating, by the relevant information graphical presentation engine, a GUI element that references the reason portion of the patient EMR and inserting, by the relevant information graphical presentation engine, the GUI element in the GUI in association with the information from the patient EMR pertinent to the outcome. The method further comprises outputting, by the relevant information graphical presentation engine, the GUI to the healthcare professional.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 4A-4E depict example graphical user interface elements for presenting relevant information from electronic medical records in accordance with an illustrative embodiment;

FIG. 8 is a flowchart illustrating operation of a mechanism for contextual EMR based graphical user interface elements in accordance with an illustrative embodiment.

DETAILED DESCRIPTION

Figure 1:
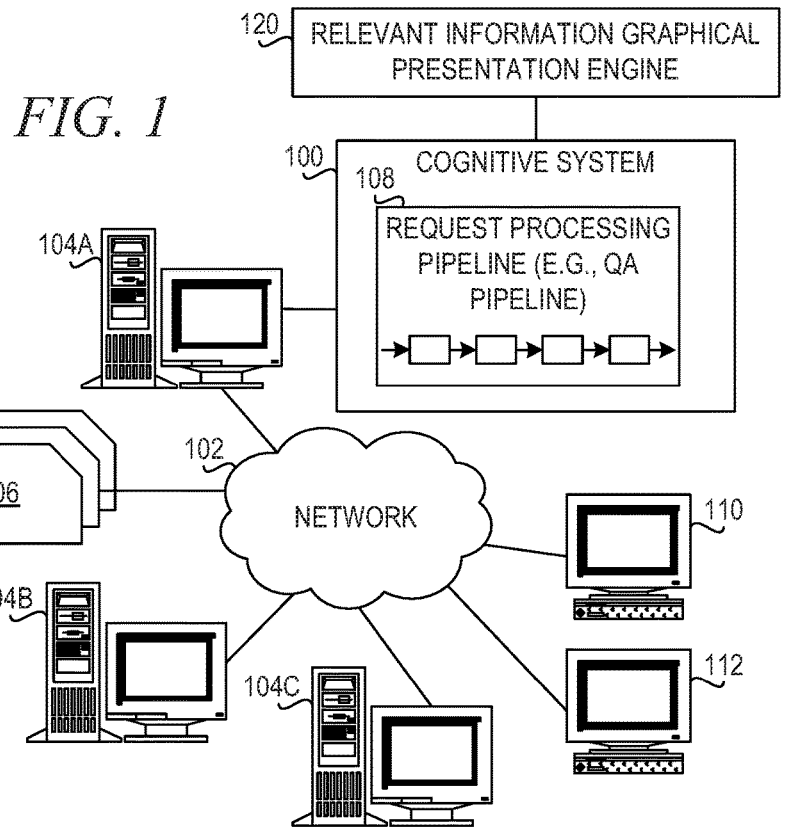
FIG. 1 depicts a schematic diagram of one illustrative embodiment of a cognitive healthcare system in a computer network.

Due to government regulations and advancement in computing technology, many professionals and organizations store patient information in electronic medical records. As the size of these electronic medical records (EMRs) increases, it becomes more difficult for medical professionals to locate and disambiguate information in the EMRs to identify the portions that are of particular relevance to the patient medical conditions being investigated by the medical professional. For example, if the medical professional is treating a patient during an office visit, the medical professional may need to look through the patient's medical history, as stored in the EMR, to identify the particular portions that are relevant to the particular medical issue that the patient is complaining of and/or identify the portions that are of particular importance to previous treatment plans that were applied to the patient. This may be a daunting task, which prior to the implementation of EMRs was a manual task, especially when integration of EMRs from a variety of different sources of information becomes more prolific. That is, when a patient's complied EMRs store information from a variety of different hospitals, pharmacies, emergency clinics, doctors, specialists, etc., it may be difficult to identify what information in these EMRs is of particular relevance to the patient's current medical issues and the particular plan of treatment previously prescribed to the patient. Thus, there is a high likelihood that some pertinent information may be missed. Moreover, the complexity of searching through EMRs to find relevant information leads to frustration on the part of the medical professional.

The illustrative embodiments provide mechanisms for providing electronic medical record (EMR) context based graphical user interface (GUI) elements in a healthcare dashboard. The GUI element is provided in association with points along a representation of a patient's treatment where changes in the patient's treatment occurred, e.g., a change in medication, dosage, etc. The GUI element allows the user to hover over or select the GUI element to obtain detailed information as to the reasoning behind the change in the patient treatment.

The illustrative embodiments alleviate the burden and frustration of a medical professional when searching through past medical information about the patient in a voluminous patient EMR to find information pertinent to understanding the reasons why a patient's treatment plan was changed.

The illustrative embodiments may aggregate information in an answer, not only from the EMR but also from other curated sources of medical knowledge (e.g., Micromedex™ from IBM Corporation or through a partnership with a third party).

Clinicians sift through EMR data to determine how to treat the patient but also to find common ground on which to build a relationship. A personal connection between the doctor and the patient is associated with higher rates of patient adherence. The illustrative embodiments find answers to the user's prototypical questions and presents the information in a way that maximizes the ability to see notable (or even remarkable) information at a glance. It is not the purpose of the illustrative embodiments to show everything, but rather only the notable information. Unlike current systems where users are overwhelmed by the amount of information being presented, the illustrative embodiments help the user focus on what is most important. That is, the information is aggregated and synthesized.

The illustrative embodiments may be used in a radiology environment and may include annotated images as an answer to a question. In addition, the illustrative embodiments may present information with nudges to help overcome clinical inertia. For example, the GUI may present the following message: "This reading has been high enough long enough." This may be based on analysis of the person's data or based on how well the patient is being managed in relation to the user's other patients or the healthcare system's patient population.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable); or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
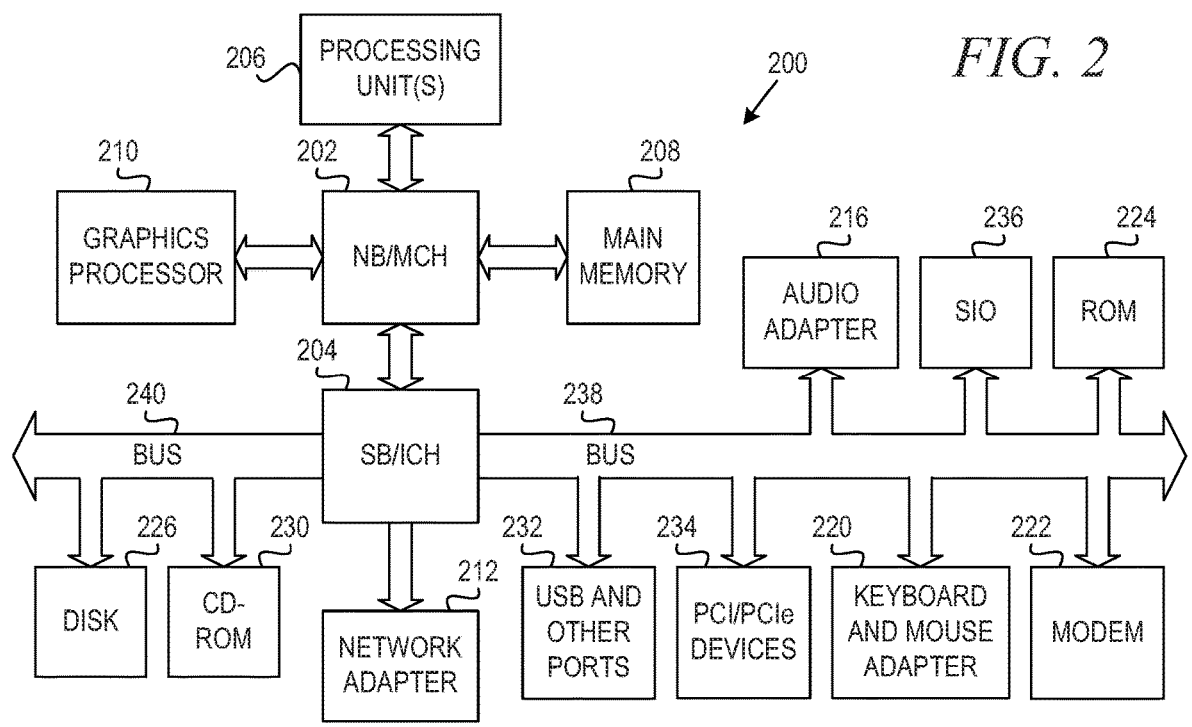
FIG. 2 is a block diagram of an example data processing system in which aspects of the illustrative embodiments are implemented.
Figure 3:
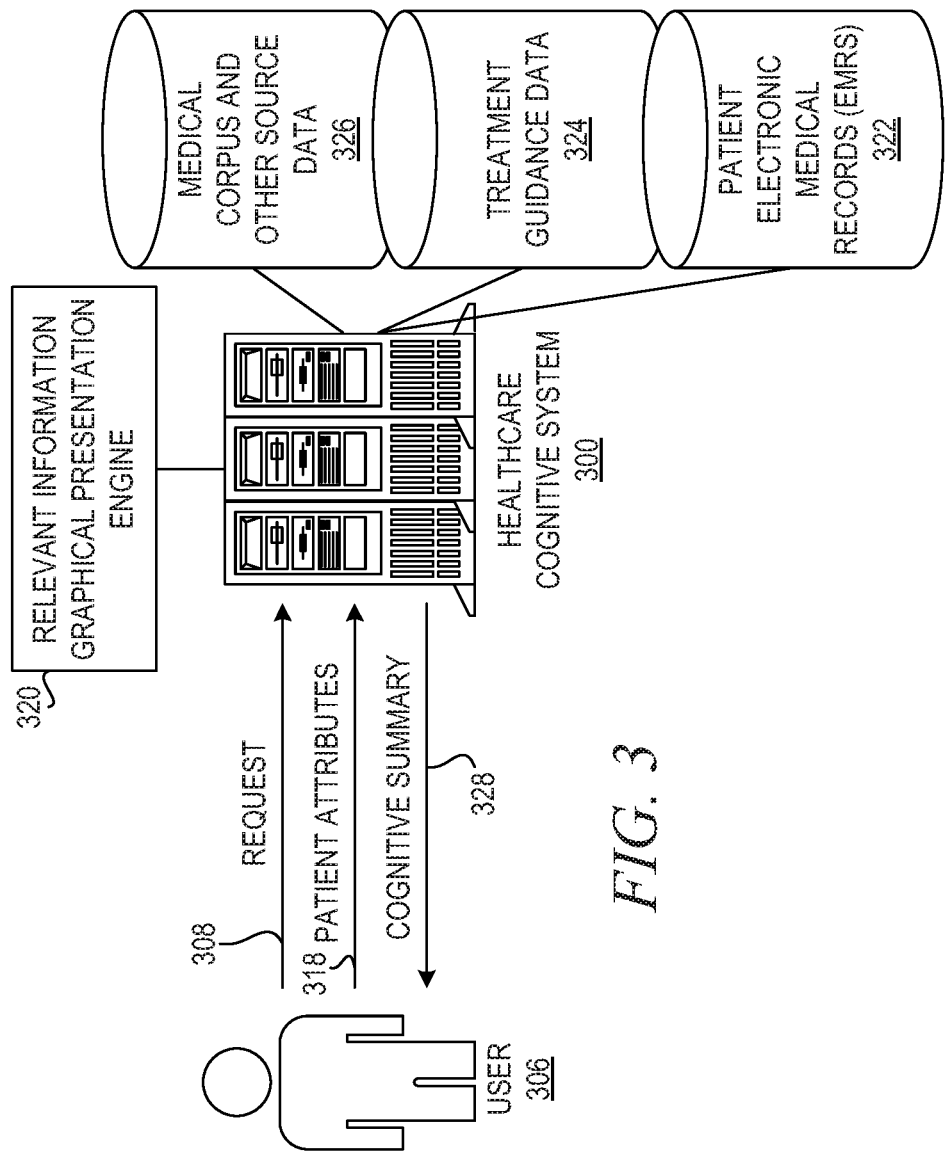
FIG. 3 is an example diagram illustrating an interaction of elements of a healthcare cognitive system in accordance with one illustrative embodiment.

As noted above, the present invention provides mechanisms for graphical presentation of relevant information from electronic medical records. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. These corpora may include, but are not limited to, EMR data. The cognitive system may determine what is important to aggregate by incorporating knowledge from a corpus of medical knowledge (e.g., curated literature, scientific articles, national guidelines, etc.). A benefit of the illustrative embodiments is to aggregate information from these multiple sources in a single timeline. Thus, the measurements included in the display are aggregated within a consistent timeline. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As will be discussed in greater detail hereafter, the illustrative embodiments may be integrated in, augment, and extend the functionality of these QA pipeline, or request processing pipeline, mechanisms of a healthcare cognitive system with regard to an electronic medical record completeness and data quality assessment mechanism.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a relevant information graphical presentation engine 120 for reducing the foraging a doctor has to do to find the information that they are looking for by providing a graphical user interface (GUI) that compiles and presents the information in such a way as to correlate relevant clinical information that is contextually relevant to the particular information that the doctor is likely attempting to view.

Relevant information graphical presentation engine 120 finds the order which questions are asked by a physician when they are caring for a patient and provides and consolidates all of the information for a single problem in one place structured in accordance with the order and importance in which the questions are asked by the physician. This is done without the clinician actually asking, e.g., by typing the questions. Instead, relevant information graphical presentation engine 120 anticipates the prototypical questions, through knowledge of the clinician's mental model, a clinician asks and provides the answers in a consolidated way. Both structured and unstructured data are presented in one place at one time in the GUI, which highlights the information for answering the prototypical questions asked by the physician and shows where the information came from.

Consider a primary care physician who is deciding which drug to try next to get a patient's blood pressure under control. Some of the prototypical questions may include the following:

What drug(s) has the patient been on in the past?
What were the drug's doses?
When did the patient stop?
Why did the patient stop?

Relevant information graphical presentation engine 120 also provides support for source of the data used in answering the question. For example, relevant information graphical presentation engine 120 may provide a link to the actual note where the clinician wrote the reason for stopping a drug, correlation of the person's current medication to recent, possibly out-of-range, lab result to show correspondence, and the like. Relevant information graphical presentation engine 120 correlates data from a variety of sources.

The prototypical questions and the information presented to answer those questions may be personalized to the user based on learned information about the way the user, or similar users, interacts with the GUI. Relevant information graphical presentation engine 120 can provide slightly more or slightly less information for the particular user depending on the user's usage patterns. Moreover, relevant information graphical presentation engine 120 may select GUI interface elements to present as part of the GUI based on changes in the patient's personalized information, including any symptoms documented by the clinician in the note, and an identification of trends of what information is presented on multiple visits by the patient. Different information may be presented dependent upon the particular medical conditions being evaluated by the user and the user may customize the presented information for the current session or for all future sessions.

The goal of relevant information graphical presentation engine 120 is to reduce the foraging a doctor has to do to find the information that he or she is looking for by making connections for the doctor as to clinically relevant information through the use of the prototypical questions. For example, a lab result may indicate that a patient has low potassium, and further analysis may indicate that the patient is on a medication that may cause the low potassium. This information may be represented in the GUI in a manner that is conspicuous to the user, thereby reducing the cognitive burden on the doctor. The GUI may also show treatments that have been tried by the current user or by others, how successful they are, and the alerts that show what might be a problem for the patient personally.

In one embodiment, relevant information graphical presentation engine 120 provides information that associates the sources of information displayed on the GUI when the user moves a cursor over that portion of the display. This information may include social and behavioral information regarding changes that occur with changes in treatment or with visits. For each disease there may be separate sets of lifestyle features that can affect the disease and the GUI correlates events with regard to these lifestyle features. For example, there may be ten lifestyle features that are relevant to a particular event, but only the ones that are relevant to the particular patient, i.e., something that has been mentioned in the patient's EMR may be represented in the display. Relevant information graphical presentation engine 120 also pulls out the lab results that are relevant to the disease and the trend of those lab results over time.

In some illustrative embodiments, relevant information graphical presentation engine 120 provides a particular ordering of sections of the GUI where a first portion of the display is the outcome the doctor is trying to measure or control, e.g., blood pressure for hypertension. A second portion of the display presents the main supporting measurements for what the doctor is doing to control the outcome, e.g., medications. A third portion of the display presents lifestyle information if the doctor is using that to try to control the condition. A fourth portion of the display presents ancillary measurements that are related to the outcome of interest, e.g., relevant laboratory results, physiological variables like weight or heart rate, etc. In addition, the display may include a portion presenting answers to other prototypical questions, such as the plan from the last visit, events that happened since the last visit, to-do lists that are guideline based for the particular disease and correlate with information in the EMR to determine if the patient is complying with these to-do items and checking to check if the patient has scheduled appointments, information indicating whether clinical inertia is evident in the management of the patient's condition and so forth.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located, in one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. The cognitive summary 328 may be presented in a ranked ordering with associated supporting evidence, obtained from the patient attributes 318 and data sources 322-326, indicating the reasoning as to why portions of EMR data 322 are being provided.

Note that EMR data 322 or data presented to the user may come from home readings or measurements that the patient makes available and are collected into EMR data 322.

In accordance with the illustrative embodiments herein, the healthcare cognitive system 300 is augmented to include a relevant information graphical presentation engine 320 to reduce the foraging a doctor has to do to find the information that the doctor is looking for by providing a graphical user interface (GUI) that compiles and presents the information in such a way as to correlate information that is contextually and clinically relevant to the particular information that the doctor is likely attempting to view. The relevant information graphical presentation engine 320 is described in further detail below.

Figure 4B:
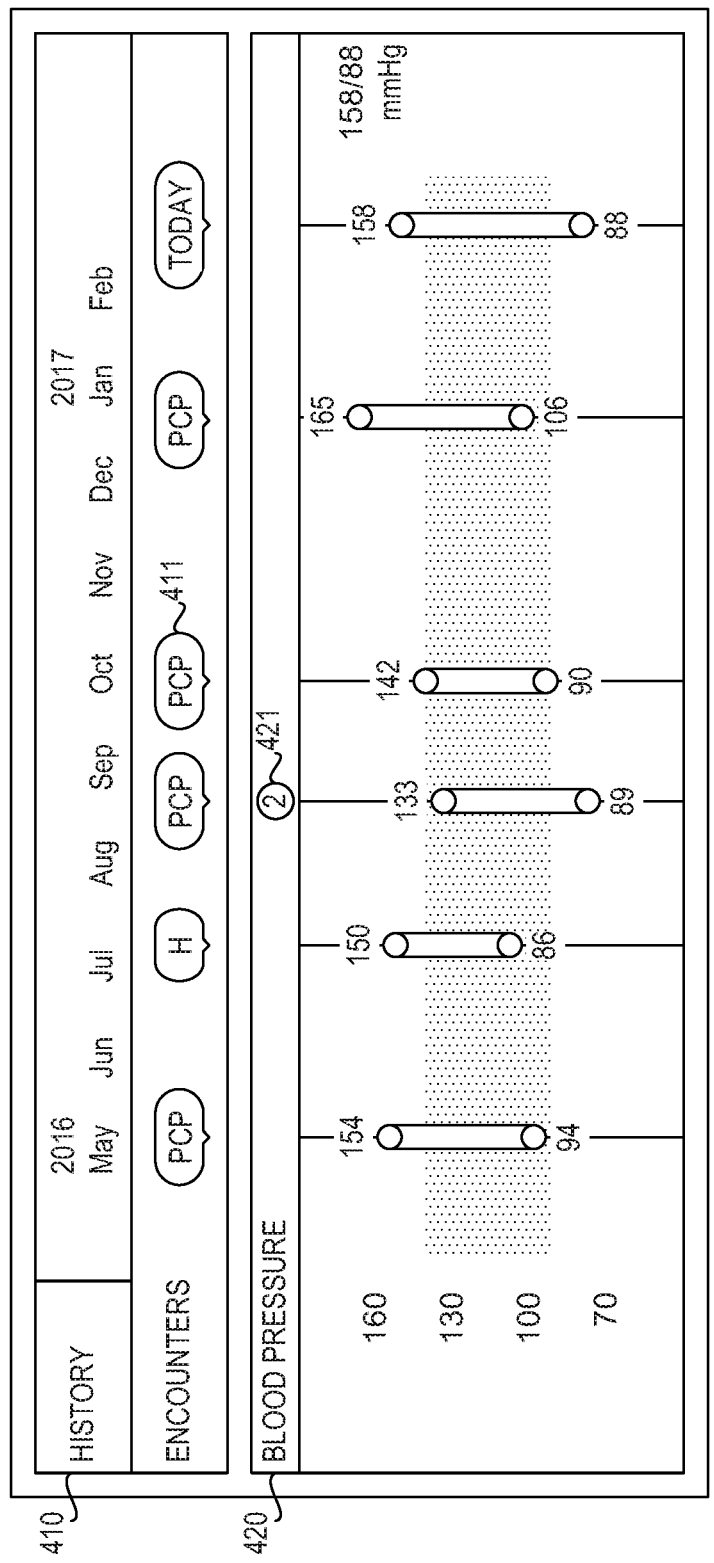
Figure 4C:
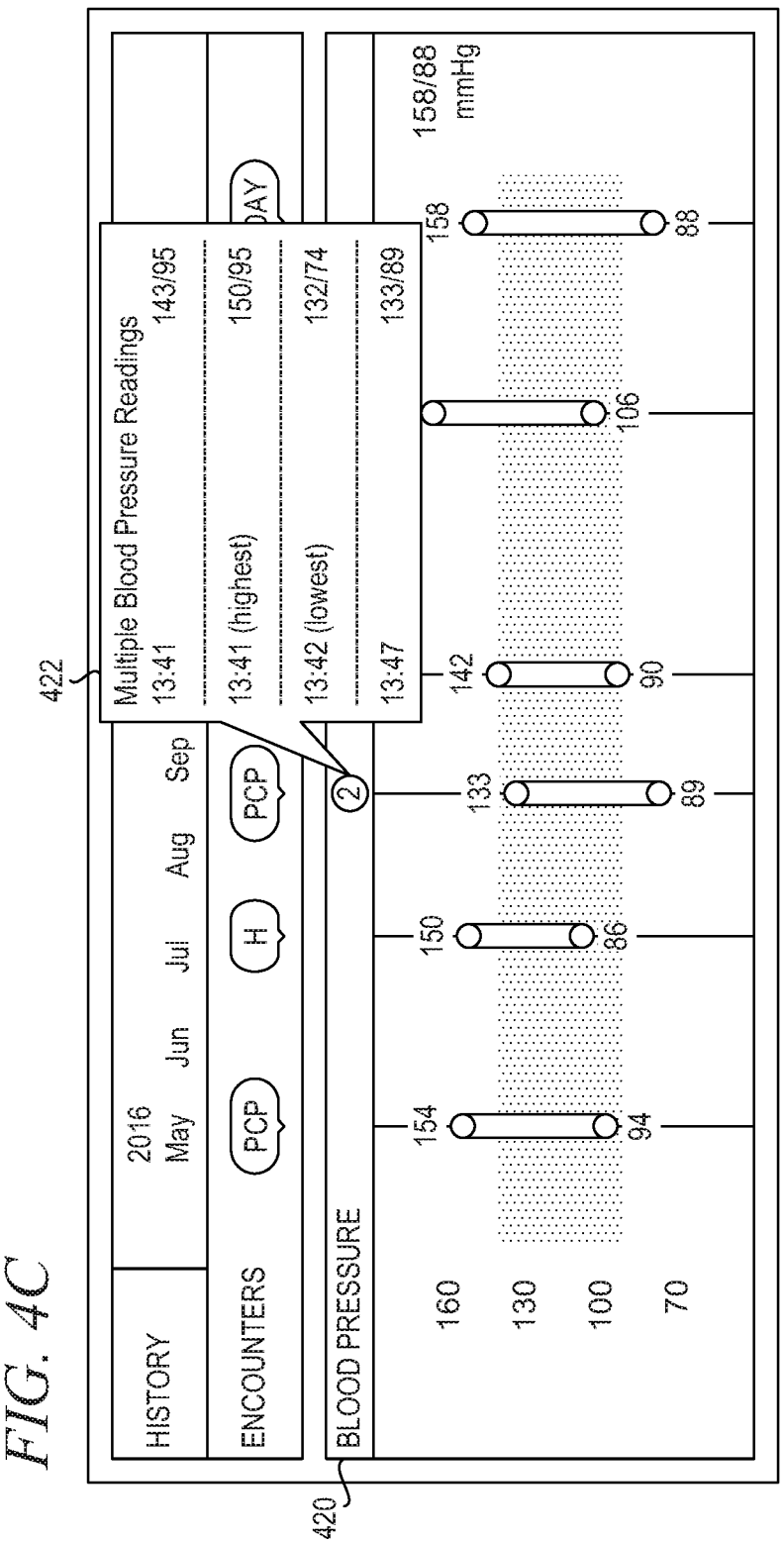

FIGS. 4A-4C depict example graphical user interface elements for presenting relevant information from electronic medical records in accordance with an illustrative embodiment. With reference to FIG. 4A, relevant information graphical user interface (GUI) 400 highlights information for answering prototypical questions and links to the source of the information. Relevant information GUI 400 includes a history portion 410 for treating a particular patient. History portion 410 presents a history timeline with indicators for encounters between the doctor and the patient. The encounters may include primary care physician office visits, hospital visits, and a current encounter with the patient. Thus, the information aggregated and synthesized within GUI 400 is presented within a consistent timeline based on history portion 410.

In accordance with an illustrative embodiment, history portion 410 presents the history timeline against which changes in patient treatment may be presented. The healthcare dashboard in GUI 400 may be augmented to include GUI elements that are EMR context based GUI elements for indicating underlying reasoning as to the change in a patient's treatment. The GUI elements that are represented in the healthcare dashboard are context based in that they are based on the particular current dashboard representation being viewed by the user and are based on the particular patient EMR data corresponding to that particular dashboard representation.

Outcome portion 420 presents the outcome the doctor is attempting to measure or control graphed along a historical timeline. Supporting measurements portion 430 presents the measurements that support what the doctor is doing to control the outcome. Lifestyle portion 440 presents lifestyle information if the doctor is using lifestyle changes to control the condition or outcome. Ancillary measurements portion 450 presents measurements that are related to the outcome of interest. All this information is overlaid along a consistent timeline.

GUI portion 401 presents answers to other prototypical questions, such as the plan from the last visit, events that happened since the last visit, to-do lists that are guideline based for the particular disease and correlate with information in the EMR to determine if the patient is complying with these to-do items and to check if the patient has scheduled appointments and such. In the example depicted in FIG. 4A, GUI portion 401 presents an answer to a prototypical question concerning a plan from the last visit.

With reference now to FIG. 4B, outcome portion 420 of the GUI is shown in association with history portion 410 along a timeline. As shown in FIG. 4B, each encounter indicator 411 is selectable to view information from the patient EMR regarding the encounter in September 2016. For instance, GUI indicator 411 is selectable to view information about that primary care physician visit relevant to hypertension. Likewise, if the user was focused on diabetes or other medical conditions, information would be presented relevant to those conditions.

In the depicted example, the outcome the doctor is attempting to control is blood pressure for hypertension. Outcome portion 410 includes a GUI element 421 indicating that there are two blood pressure (BP) readings associated with the primary care physician visit in August 2016. GUI element 421 is selectable by the user to view information from the EMR regarding the two BP readings. An insight might also be presented from the EMR providing information explaining why more than one reading was taken.

In accordance with the illustrative embodiment, the relevant information graphical presentation engine may note that blood pressure was under control for the August 2016 encounter. The relevant information graphical presentation engine may determine prototypical questions for such an event. For example, the relevant information graphical presentation engine may ask the following questions:

What were the BP readings?
What medication was the patient taking?
What was the patient's weight?
What was the plan during the last visit?
Did the patient follow the plan?

The relevant information graphical presentation engine selects prototypical questions according to the user's learned usage patterns and submits the selected questions to the healthcare cognitive system, which in turn finds answers to the selected questions in the patient's EMR. As an example, the relevant information graphical presentation engine may select the prototypical question, "What were the BP readings?" The relevant information graphical presentation engine then receives the answer from the healthcare cognitive system and generates GUI element 421, which is selectable by the user to view the answer. The user may select GUI element 421 by mouse clicking on the element, tapping on it (in a touch UI)), or by making a mouseover interaction.

Turning to FIG. 4C, in response to the user selecting the GUI element 421, the relevant information graphical presentation engine presents answer GUI element 422, which displays the answer content from the EMR. Thus, the relevant information graphical presentation engine anticipates a prototypical question the doctor may ask given the information displayed in the GUI, obtains an answer to the question, and presents the answer content from the patient's EMR in association with the information about which the question was asked.

Figure 4D:
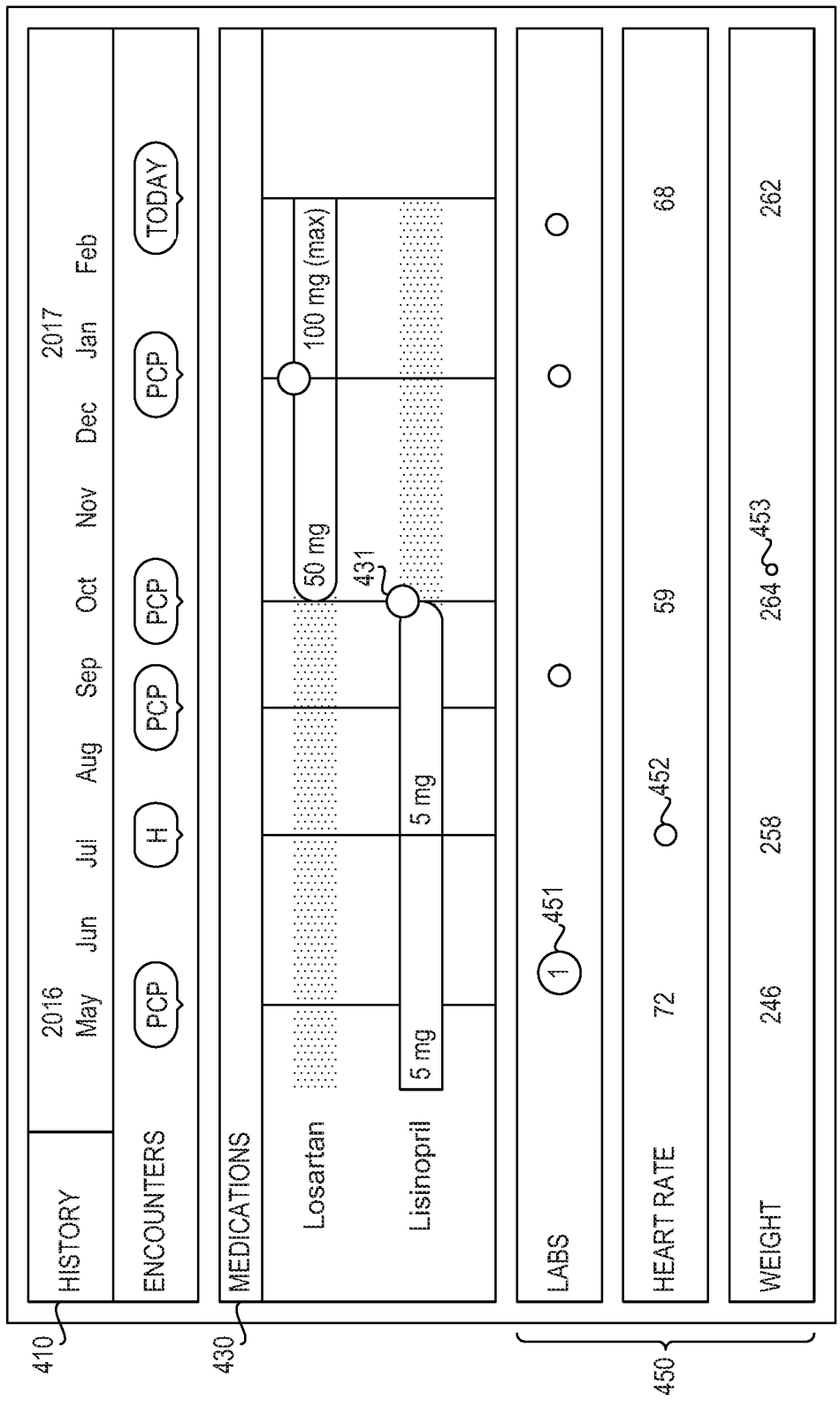

With reference now to FIG. 4D, supporting measurements portion 430 of the GUI is shown in association with history portion 410. In the depicted example, supporting measurement portion 430 presents medications used to control the patient's blood pressure. The relevant information graphical presentation engine selects the prototypical question, "What medication is the patient taking?" The relevant information graphical presentation engine submits the question to the healthcare cognitive system, which returns the information from the patient's EMR presented in support measurements portion 430.

In the depicted example, the patient's medications under a treatment plan are currently being viewed in the dashboard, and GUI element 431 is associated with the point in time along the timeline 410 where the patient's medication was changed in some way, e.g., different medication, new medication, new dosage, termination of the medication, etc.

As shown in FIG. 4D, the patient stopped taking Lisinopril and started taking Losartan. The relevant information graphical presentation engine selects the prototypical question, "Why did the patient stop taking Lisinopril?" The relevant information graphical presentation engine submits the question to the healthcare cognitive system, which returns an answer from the patient's EMR. The relevant information graphical presentation engine generates GUI element 431, which is selectable by the user to view the answer.

In the example depicted in FIG. 4D, the change in treatment plan is a change in medication or the termination of the medication Lisinopril. The prototypical question asked is the reasoning behind changing the treatment plan.

Ancillary measurements portions 450 include labs portion, heart rate portion, and weight portion. The labs portion includes a lab result with one lab out of range. The relevant information graphical presentation engine generates GUI element 451, which is selectable by the user to view an answer to a prototypical question about the out-of-range lab result. In the heart rate portion, the relevant information graphical presentation engine generates GUI element 452, which is selectable by the user to view an answer to a prototypical question about a given heart rate reading. In the weight portion, the relevant information graphical presentation engine generates GUI element 453, which is selectable by the user to view an answer to a prototypical question about a given weight measurement.

Turning to FIG. 4E in response to the user selecting the GUI element 431, the relevant information graphical presentation engine presents answer GUI element 432, which displays the answer content from the EMR about why the user stopped taking Lisinopril, Thus, the relevant information graphical presentation engine anticipates a prototypical question the doctor may ask given the information displayed in the GUI, obtains an answer to the question, and presents the answer content from the patient's EMR in association with the information about which the question was asked. The information will also include a link back to read the original note from which the insight was extracted.

The GUI elements may also include present information with nudges to help overcome clinical inertia. For example, a GUI element may present the following message: "This reading has been high enough long enough." This may be presented in a GUI portion adjacent to the current treatment plan or elsewhere. The information may be based on analysis of the patient's data or based on how well the patient is being managed relative to the user's other patients or the healthcare system's patient population.

GUI element 431 provides a linkage to portions of content in the patient's EMR data that indicate reasons as to the change in treatment. The association of these portions with the change in treatment may be determined from natural language processing and cognitive analysis of the EMR data with regard to the particular change in treatment. For example, if it is determined that the patient's medication changed, then physician notes in the patient EMR data that reference the medication, reference the time/day around when the medication changed, reference the medical conditions for which the medication is used as a treatment, etc. may be identified and associated with the GUI element 431. Different treatment contexts may be associated with different changes with portions of a patient's EMR data. For example, for a physical activity treatment plan for weight loss, changes in exercises to be performed, changes in frequency or intensity of exercise, etc. may be correlated with portions of the EMR data and associated with a GUI element in the corresponding representation in the healthcare dashboard.

When the user hovers over or otherwise selects the GUI element, the physician notes and portions of the EMR data pertinent to the particular change in treatment may be automatically made visible to the user, provided in a pop-up window 432 or otherwise made accessible to the user.

Figure 5:
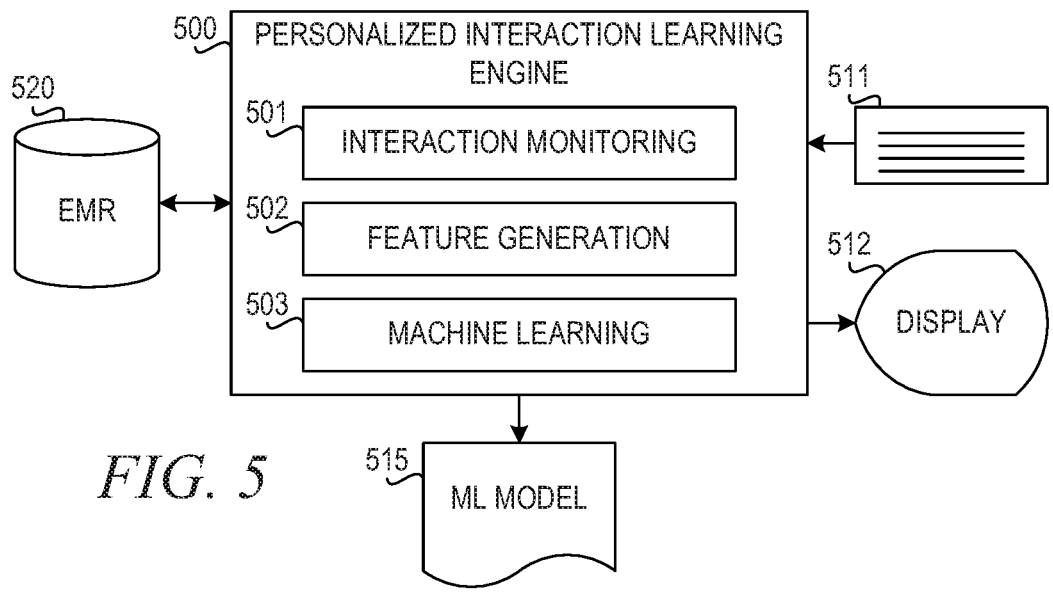
FIG. 5 is a block diagram illustrating a personalized interaction learning engine in accordance with an illustrative embodiment.

FIG. 5 is a block diagram illustrating a personalized interaction learning engine in accordance with an illustrative embodiment. Personalized interaction learning engine 500 includes interaction monitoring component 501, feature generation component 502, and machine learning component 503. Interaction monitoring component 501 monitors a user interacts with electronic medical records 520 using input devices 511 and display 512. Input devices 511 may include a keyboard, a mouse, or other known or future input devices. As the user interacts with EMR data 520, interaction monitoring component 501 detects information, such as questions asked by the user, which portions of the EMR the user views, the order in which the user asks questions, the order in which the user views EMR portions, etc.

Feature generation component 502 extracts features from the user's usage patterns from interaction monitoring component 501 and generates features for machine learning component 503. Based on the features from feature generation component 502, machine learning component 503 generates machine learning model 515. In one embodiment, machine learning model 515 is a linear regression machine learning model. However, other machine learning techniques may be used within the spirit and scope of the present invention.

Figure 6:
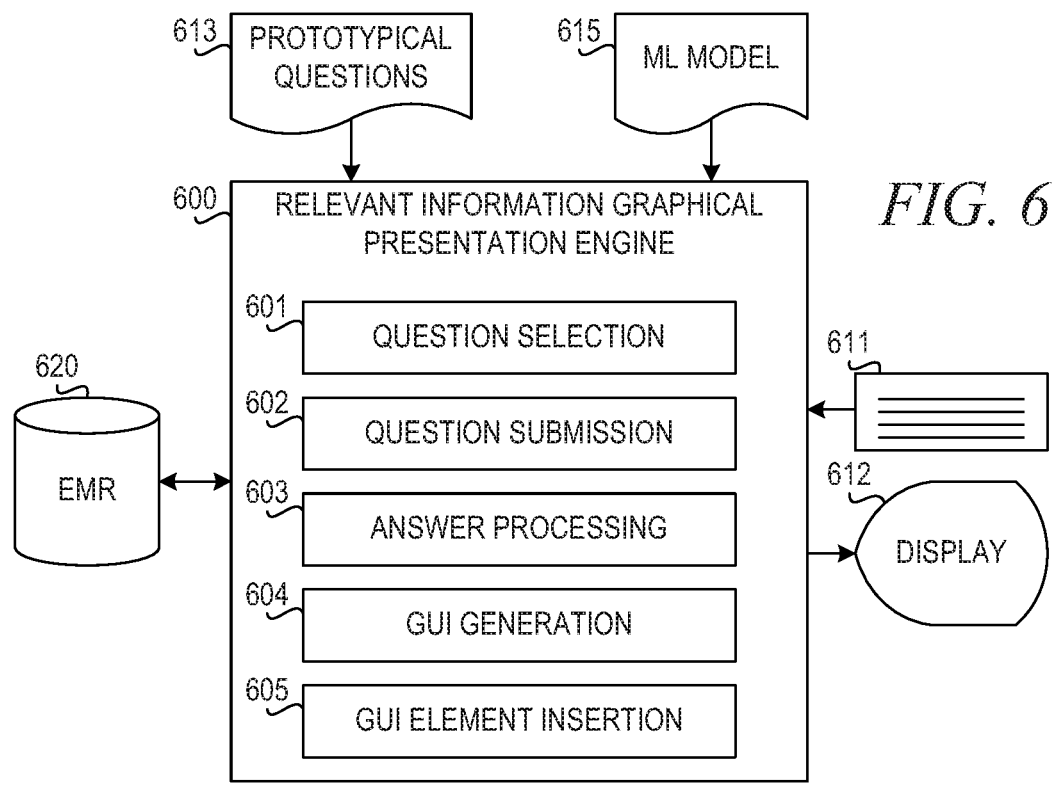
FIG. 6 is a block diagram illustrating a relevant information graphical presentation engine in accordance with an illustrative embodiment.

FIG. 6 is a block diagram illustrating a relevant information graphical presentation engine in accordance with an illustrative embodiment. Relevant information graphical presentation engine 600 includes question selection component 601, question submission component 602, answer processing component 603, GUI generation component 604, and GUI element insertion component 605. Question selection component 601 selects questions from prototypical questions 613 based on machine learning (ML) model 615 in association with a given patient and a given outcome the doctor is attempting to control. For example, if the doctor is seeing a patient for hypertension, then question selection component 601 may select prototypical questions concerning what outcome the doctor is likely to be attempting to control for hypertension, what supporting measurements are pertinent for the outcome, whether the doctor recommended a plan for controlling the outcome in a previous encounter, whether the patient is following the plan, and so forth.

Prototypical questions 613 may be provided by subject matter experts (SMEs) or may be learned from ethnographic research monitoring interactions of the user or similar users. In accordance with the illustrative embodiment, question selection component 601 selects questions without the user actually asking, e.g., by typing the questions using input device 611. Instead, question selection component 601 anticipates the prototypical questions the doctor is likely to ask based on ML model 615 and the given patient and the given outcome the doctor is attempting to control. ML model 615 may be trained by monitoring interactions of the user as described above with reference to FIG. 5.

Questions election component 601 may also select questions from prototypical questions 613 that are pertinent to the patient data displayed in the graphical user interface on display 612. For example, if the GUI is displaying heart rate information, then question selection component 601 may select prototypical questions about why a particular heart rate reading is out of range. If the GUI is displaying weight measurements, then question selection component 601 may select prototypical questions about lifestyle information, whether a diet plan was discussed during a previous encounter, or whether the patient is following a previous recommendation to increase exercise.

Question submission component 602 submits the selected prototypical questions to receive answers from the patient's EMR data. 620 and other medical corpora. In one embodiment, question submission component 602 submits the questions to a healthcare cognitive system, which then processes the questions using natural language processing (NLP) techniques. In another embodiment, question submission component 602 performs question decomposition and query formulation in a manner similar to a question answering system and submits the queries to EMR database 620.

Answer processing component 603 receives the answers to the selected prototypical questions. The answers contain information from EMR data 620 for the patient. Answer processing component 603 processes the answers by identifying portions of the EMR data that confidently answer the questions and generating links back to the EMR data 620. This helps the user better understand the source of the answer.

GUI generation component 604 generates graphical user interface portions to present EMR data relevant to the patient and an outcome the doctor is attempting to control. GUI generation component 604 also generates GUI elements for linking the patient EMR data to answers to prototypical questions from the patient EMR data 620 or other medical corpora. The GUI elements may be user selectable for presenting portions of EMR data 620. For example, the GUI elements may present EMR data in response to the user performing a mouseover operation or the like.

GUI element insertion component 605 inserts the GUI elements in the graphical user interface in association with the EMR data displayed. In this way, GUI element insertion component 605 inserts the GUI elements so as to present relevant clinical information. For example, if the GUI presents EMR data about medications being taken by the patient and the patient stopped taking a first medication and started taking a second medication, then the GUI element insertion component 605 may insert a GUI element in association with the event of the patient stopping the first medication. The implicit prototypical question is, "Why did the patient stop taking the first medication?" The answer from the patient EMR data 620 may concern a side effect of the first medication, a dry cough. The GUI element may be a user selectable element that links to EMR data 620 containing the answer to the question. GUI element insertion component 605 inserts the GUI element in association with the patient stopping the first medication within the GUI. Thus, the user perceives the information in a manner that is conspicuous to the user, the effect being the patient stopping the first medication and the cause being the side effect.

In one embodiment, relevant information graphical presentation engine 600 augments a healthcare dashboard to include GUI elements that are EMR context based for indicating underlying reasoning as a change in a patient's treatment. GUI generation component 604 generates GUI elements that are context based in that they are based on the particular current dashboard representation being viewed by the user and are based on the particular patient EMR data 620 corresponding to that particular dashboard representation.

Relevant information graphical presentation engine 600 detects a change in treatment, and question selection component 601 selects prototypical questions 613 with respect to the reasons for the change in treatment. Question submission component 602 then submits the questions, and answer processing component 603 identifies the portions of EMR 620 that answer the questions and provide reasoning for the change in treatment.

GUI generation component 604 generates GUI elements that provide a linkage to portions of content in the patient's EMR data 620 that indicate reasons as to the change in treatment. The association of these portions with the change in treatment may be determined from natural language processing and cognitive analysis of the EMR data 620 with regard to the particular change in treatment. Different treatment contexts may be associated with different changes with portions of a patient's EMR data 620. When the user hovers over or otherwise selects the GUI element, the physician notes and portions of the EMR data 620 pertinent to the particular change in treatment may be automatically made visible to the user provided in a pop-up window or otherwise made accessible to the user.

Figure 7:
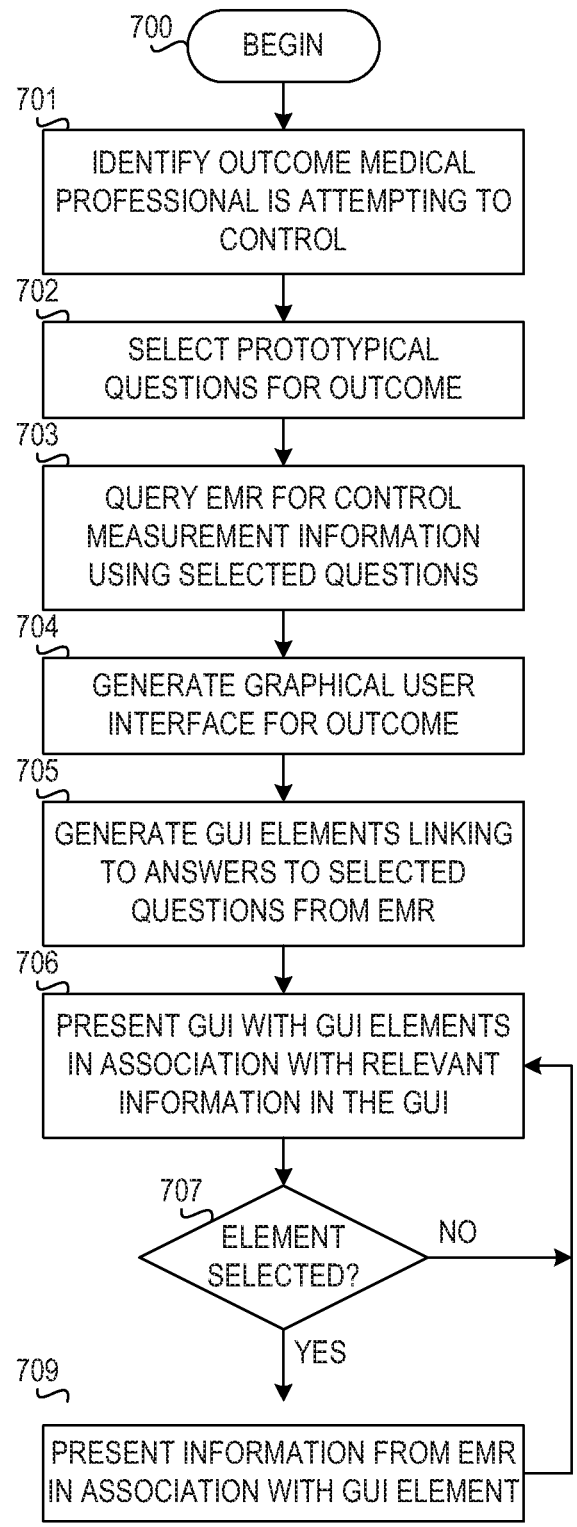
FIG. 7 is a flowchart illustrating operation of a mechanism for relevant information graphical presentation in accordance with an illustrative embodiment.

FIG. 7 is a flowchart illustrating operation of a mechanism for relevant information graphical presentation in accordance with an illustrative embodiment. Operation begins (block 700), and the mechanism identifies an outcome the medical professional is attempting to control (block 701). The mechanism selects prototypical questions for the outcome (block 702) and queries the electronic medical record (EMR) for control measurement information using the selected questions (block 703). In one embodiment, the mechanism may also query a medical information system and bring additional information to help answer the question. The medical information system may provide drug-related information or the like. Thus, block 703 may include extracting data from the EMR as well as retrieving information from a corpus of curated medical literature.

The method generates a graphical user interface (GUI) for the outcome the medical professions is attempting to control (block 704). The mechanism then generates GUI elements linking to the answers to the selected questions from the EMR (block 705). The mechanism presents the GUI with the GUI elements inserted in association with the relevant information of the GUI. (block 706).

The mechanism determines whether the user selects a given GUI element (block 707). The user may select a GUI element using a mouse click or mouseover action, for example. If the user selects a given GUI element, then the mechanism presents the information from the EMR in association with the GUI element (block 709). Thereafter, or if the user does not select a given GUI element in block 707, operation returns to block 706 to present the GUI.

FIG. 8 is a flowchart illustrating operation of a mechanism for contextual EMR based graphical user interface elements in accordance with an illustrative embodiment. Operation begins (block 800), and the mechanism generates a timeline of treatment for the patient from electronic medical record (EMR) data (block 801). The mechanism then identifies a change in treatment in the patient EMR (block 802). The change in treatment may be, for example, a different medication, a new medication, a new dosage, termination of a medication, change in suggested exercise frequency or intensity, change in exercises to be performed or duration of exercise, dietary changes, or the like.

The mechanism queries the patient EMR for reasons for the changes in treatment (block 803). In one embodiment, the mechanism selects prototypical questions concerning the reasoning for the changes in treatment. The mechanism then submits the questions to a cognitive system, such as a question answering system, which identifies passages from the patient EMR that are likely to be correct answers to the submitted questions. The mechanism then receives the identified passages from the patient EMR as answers to the submitted questions.

The mechanism generates graphical user interface (GUI) elements linking to the reasons for changes in treatment from the patient EMR (block 804). The mechanism then presents the graphical user interface with the GUI elements at points in the timeline corresponding to the changes in treatment (block 805). The mechanism determines whether the user selects a given GUI element (block 806). The user may select a GUI element using a mouse click or mouseover action, for example. If the user selects a given GUI element, then the mechanism presents the information from the EMR in association with the GUI element (block 807). Thereafter, or if the user does not select a given GUI element in block 806, operation returns to block 805 to present the GUI.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art, to understand the embodiments disclosed herein.

What is claimed is:

1. A method, in a data processing system comprising a processor and a memory, the memory comprising instructions that are executed by the processor to specifically configure the processor to implement a relevant information graphical presentation engine for providing a graphical user interface (GUI) that presents information from a patient electronic medical record (EMR), the method comprising:
   generating, by a graphical user interface generation component executing within the relevant information graphical presentation engine, a GUI presenting patient EMR data pertinent to a condition of the patient;
   identifying, by the relevant information graphical presentation engine, a change in treatment recorded in the patient EMR;
   selecting, by a question selection component executing within the relevant information graphical presentation engine, a question from a set of prototypical questions corresponding to the change in treatment using a trained machine learning model;
   submitting, by a question submission component executing within the relevant information graphical presentation engine, the selected question to a healthcare cognitive system to query the patient EMR for a reason for the change in treatment;
   receiving, by an answer processing component executing within the relevant information graphical presentation engine, at least one answer from the healthcare cognitive system identifying of a reason portion of the patient EMR that provides a reason for the change in treatment;
   generating, by a GUI element insertion component executing within the relevant information graphical presentation engine, a GUI element that links to the reason portion of the patient EMR;
   inserting, by the GUI element insertion component, the GUI element in the GUI in association with the information from the patient EMR pertinent to the change in treatment;
   outputting, by the relevant information graphical presentation engine, the GUI to the healthcare professional; and
   presenting, by the relevant information graphical presentation engine, the reason portion of the patient EMR responsive to user selection of the GUI element.

2. The method of claim 1, wherein the GUI comprises a treatment timeline.

3. The method of claim 2, wherein inserting the GUI element in the GUI comprises inserting the GUI element in the treatment timeline at a point corresponding to a time of the change in treatment.

4. The method of claim 1, wherein the user selection comprises a mouseover operation or a mouse click operation.

5. The method of claim 1, wherein presenting the reason portion of the patient EMR comprises presenting a pop-up window containing information derived from the reason portion of the patient EMR.

6. The method of claim 5, wherein the pop-up window presents a link to the reason portion of the patient EMR.

7. A computer program product comprising a computer readable storage medium having a computer readable program stored therein, wherein the computer readable program, when executed on at least one processor of a data processing system, causes the data processing system to implement a relevant information graphical presentation engine for providing a graphical user interface (GUI) that presents information from a patient electronic medical record (EMR), wherein the computer readable program causes the data processing system to:
generate, by a graphical user interface generation component executing within the relevant information graphical presentation engine, a GUI presenting patient EMR data pertinent to a condition of the patient;
identify, by the relevant information graphical presentation engine, a change in treatment recorded in the patient EMR;
select, by a question selection component executing within the relevant information graphical presentation engine, a question from a set of prototypical questions corresponding to the change in treatment using a trained machine learning model;
submit, by a question submission component executing within the relevant information graphical presentation engine, the selected question to a healthcare cognitive system to query the patient EMR for a reason for the change in treatment;
receive, by an answer processing component executing within the relevant information graphical presentation engine, at least one answer from the healthcare cognitive system identifying of a reason portion of the patient EMR that provides a reason for the change in treatment;
generate, by a GUI element insertion component executing within the relevant information graphical presentation engine, a GUI element that links to the reason portion of the patient EMR;
insert, by the GUI element insertion component, the GUI element in the GUI in association with the information from the patient EMR pertinent to the change in treatment;
output, by the relevant information graphical presentation engine, the GUI to the healthcare professional; and
present, by the relevant information graphical presentation engine, the reason portion of the patient EMR responsive to user selection of the GUI element.

8. The computer program product of claim 7, wherein the GUI comprises a treatment timeline.

9. The computer program product of claim 8, wherein inserting the GUI element in the GUI comprises inserting the GUI element in the treatment timeline at a point corresponding to a time of the change in treatment.

10. The computer program product of claim 7, wherein the user selection comprises a mouseover operation or a mouse click operation.

11. The computer program product of claim 7, wherein presenting the reason portion of the patient EMR comprises presenting a pop-up window containing information derived from the reason portion of the patient EMR.

12. The computer program product of claim 11, wherein the pop-up window presents a link to the reason portion of the patient EMR.

13. An apparatus comprising:
a processor; and
a memory coupled to the processor, wherein the memory comprises instructions which, when executed by the processor, cause the processor to implement a relevant information graphical presentation engine for providing a graphical user interface (GUI) that presents information from a patient electronic medical record (EMR), wherein the instructions cause the processor to:
generate, by a graphical user interface generation component executing within the relevant information graphical presentation engine, a GUI presenting patient EMR data pertinent to a condition of the patient;
identify, by the relevant information graphical presentation engine, a change in treatment recorded in the patient EMR;
select, by a question selection component executing within the relevant information graphical presentation engine, a question from a set of prototypical questions corresponding to the change in treatment using a trained machine learning model;
submit, by a question submission component executing within the relevant information graphical presentation engine, the selected question to a healthcare cognitive system to query the patient EMR for a reason for the change in treatment;
receive, by an answer processing component executing within the relevant information graphical presentation engine, at least one answer from the healthcare cognitive system identifying of a reason portion of the patient EMR that provides a reason for the change in treatment;
generate, by a GUI element insertion component executing within the relevant information graphical presentation engine, a GUI element that links to the reason portion of the patient EMR;
insert, by the GUI element insertion component, the GUI element in the GUI in association with the information from the patient EMR pertinent to the change in treatment;
output, by the relevant information graphical presentation engine, the GUI to the healthcare professional; and
present, by the relevant information graphical presentation engine, the reason portion of the patient EMR responsive to user selection of the GUI element.

14. The apparatus of claim 13, wherein the GUI comprises a treatment timeline.

15. The apparatus of claim 14, wherein inserting the GUI element in the GUI comprises inserting the GUI element in the treatment timeline at a point corresponding to a time of the change in treatment.

16. The apparatus of claim 13, wherein the user selection comprises a mouseover operation or a mouse click operation.

17. The apparatus of claim 13, wherein presenting the reason portion of the patient EMR comprises presenting a pop-up window containing information derived from the reason portion of the patient EMR.

18. The method of claim 1, wherein the set of prototypical questions is learned by a personalized interaction learning engine based on user input of questions and interaction patterns.

19. The method of claim 1, wherein the trained machine learning model is trained by a personalized interaction learning engine based on features derived from previous interaction patterns and questions entered by a user.

20. The method of claim 1, wherein the healthcare cognitive system processes the selected question using natural language processing techniques.

* * * * *